United States Patent [19]

Gordon et al.

[11] Patent Number: 5,692,510
[45] Date of Patent: Dec. 2, 1997

[54] DETERMINING CORONARY BLOOD FLOW BY CARDIAC THERMOGRAPHY IN OPEN CHEST CONDITIONS

[75] Inventors: Naama Gordon, Ramat Efal; Rafael Beyar; Samuel Sideman, both of Haifa, all of Israel

[73] Assignee: Technion Research And Development Foundation Ltd., Haifa, Israel

[21] Appl. No.: 524,843

[22] Filed: Sep. 7, 1995

[51] Int. Cl.$^6$ ............................................. A61B 6/00
[52] U.S. Cl. ................ 128/654; 128/664; 128/668; 128/736; 73/861.95
[58] Field of Search .................... 128/664, 666, 128/668, 691, 736, 633, 654; 73/861.5, 861.95

[56] References Cited

U.S. PATENT DOCUMENTS 4,995,398  2/1991  Turnidge .............................. 128/668
5,375,603  12/1994  Feiler .................................. 128/664

*Primary Examiner*—Ruth S. Smith
*Attorney, Agent, or Firm*—Mark M. Friedman

[57] ABSTRACT

Methods for determining the flow rate of a substance within an object by extracting and mathematically manipulating numerical parameters from a thermoimaging temperature response curve of the surface of the object. The methods of the present invention are suitable to determine coronary arteries flow rates and myocardial perfusion rates in open chest conditions.

37 Claims, 9 Drawing Sheets

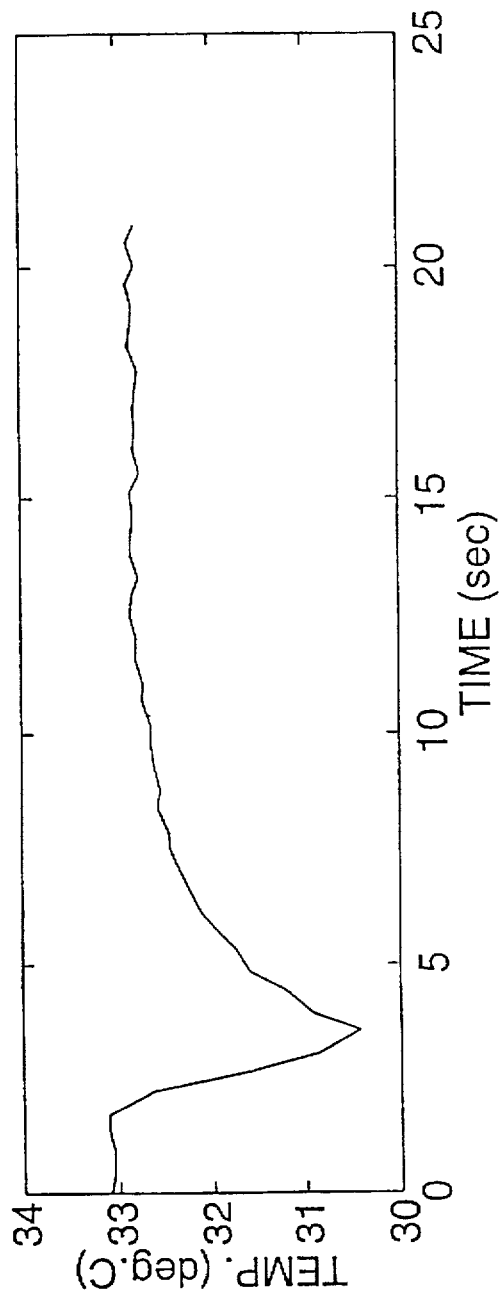
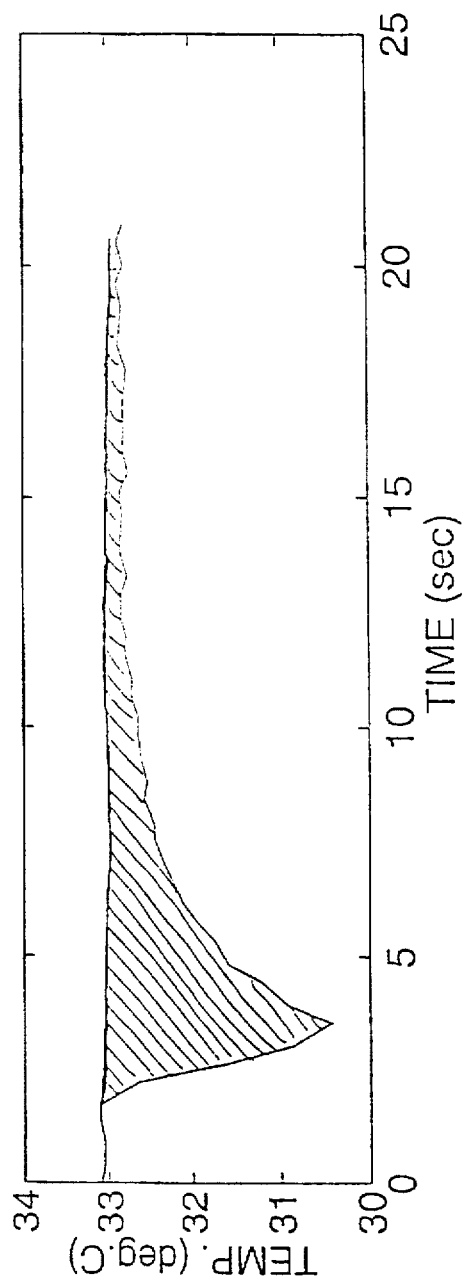
FIG. 3
FIG. 4

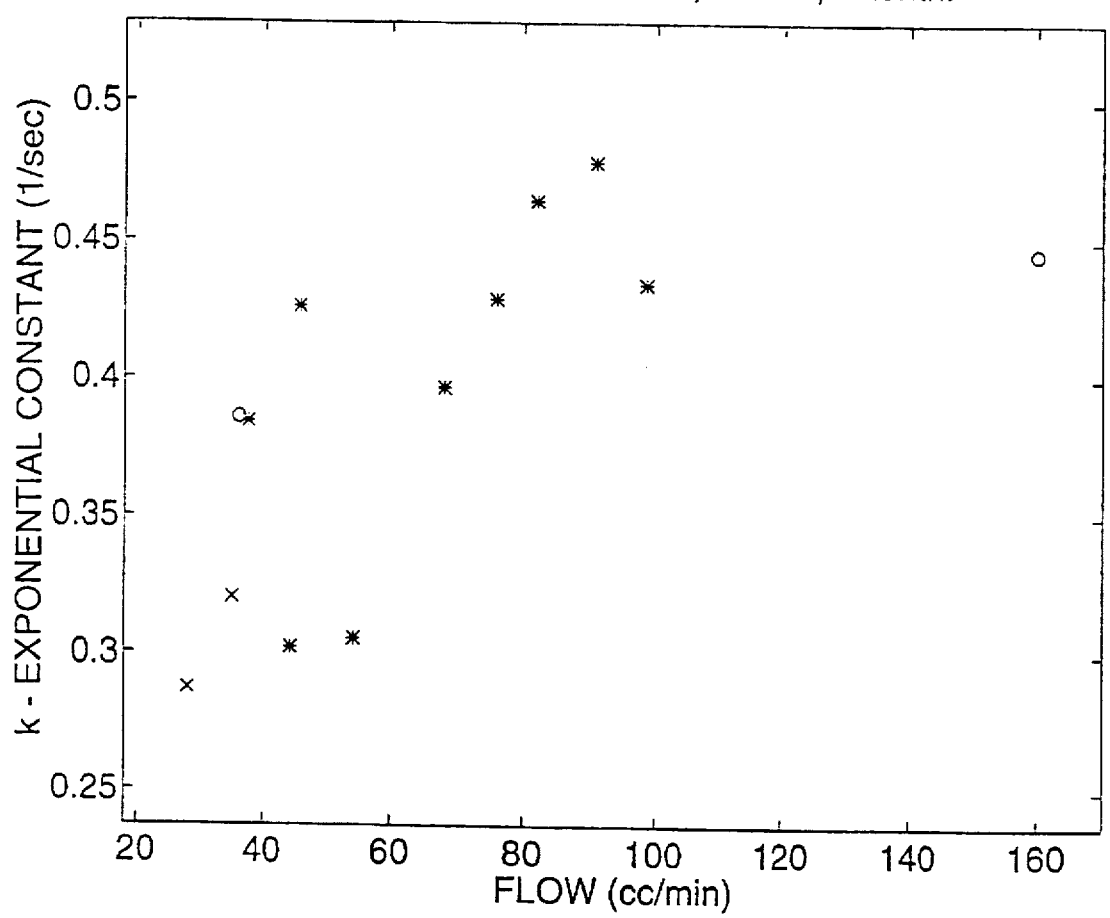

DETERMINING CORONARY BLOOD FLOW BY CARDIAC THERMOGRAPHY IN OPEN CHEST CONDITIONS

FIELD AND BACKGROUND OF THE INVENTION

The present invention relates to methods for determining flow rates of substances by thermoimaging and, more particularly, to methods for calculating flow rates of substances within objects by extracting and mathematically manipulating numerical parameters from thermoimaging transient temperature response curves of the surface of the objects.

The methods of the present invention are suitable, for example, to determine coronary flow rates and myocardial perfusion rates in open chest conditions, that is, to calculate flow rates of substances along the coronary arteries and, myocardial perfusion rates of the substances into the heart tissue, by extracting and mathematically manipulating numerical parameters from thermoimaging transient temperature response curves of the coronary arteries or a specific part of an artery and, of the heart tissue or a specific part of the heart tissue, respectively.

Availability of real-time information regarding coronary flow and myocardial perfusion may be of great value for the cardiac surgeon. For example, during the course of by-pass heart surgery, such data may be exploited for (1) deciding which regions of the coronary arteries are narrowed and, therefore, are to be by-passed; and (2) checking the successfulness of each by-pass graft, before closing the chest cavity.

Methods aimed at flow rates measurements may be divided into two major groups.

The first group of methods aimed at flow rates measurements include methods in which a detection probe is made in direct contact with the substance, which substance flow being measured, therefore, methods associated with this group are generally termed invasive methods. An example of an invasive method is the thermodilution method, in which an invasive temperature detection probe is made in direct contact with the substance which flow being measured. The invasive methods suffer two major drawbacks for application in human diagnostics, the first is their invasiveness and, the second is their ability to record data from one or at the most only few locations at a given time.

The second group of methods aimed at flow rates measurements include non-invasive methods, therefore, methods associated with this group are generally termed imaging methods.

Various non-invasive imaging methods were developed for different applications in human diagnostics as well as in other fields. A common feature characterizing these methods is the use of a contrast agent, which agent is being traced. Imaging methods used primarily for diagnostic purposes include, for example, (1) X-ray based imaging methods in which X-rays are used to detect either an internal body anatomy, such as bones in a simple X-ray analysis or, an administrated radiopaque contrast agent (e.g., iodine) used in CT and, other X-ray based imaging methods; (2) Ultrasound based imaging methods in which ultrasonic waves are used to detect either an internal body anatomy in simple ultrasound analysis or, an administrated contrast agent, such as micro-bubbles, used in contrast-echo. Yet, in other imaging methods in medicine and other fields, radioactive materials are employed as detectable agents, which materials may be detected by, for example, various kinds of radioactivity counters.

However, while using imaging methods for flow rate determination of bodily fluids, such as blood, within the body, the flow rate of the blood containing an external contrast agent provided into the body or into a specific organ in an upstream region is measured.

The methods described hereinabove, in which external contrast agents are traced, suffer a major drawback when employed for medical purposes, since in the course of their application, an external contrast agent, some times poisonous or with yet undetermined commulative effects is administrated to the human body.

Thermoimaging is an imaging method suitable for flow measurements and is devoid of all the above mentioned limitations, when employed for medical purposes. Thermoimaging is an InfraRed waves based method for detecting heat, which is, therefore, employed as a contrast agent, termed hereinbelow a thermo-contrast agent. Since the contrast agent used for thermoimaging is heat, the method is safer to the patient. Thermography is a thermoimaging method generally used for estimate flow rates of bodily fluids, such as blood, employing a thermal (i.e., InfraRed) camera, focused on an examined body organ and, a digital image processor which provides images of the organ with high spatial (ca. 0.75 mm) and thermal (0.1° C.) resolution, which images can be displayed on a high resolution monitor, in real-time. When thermography is used to estimate blood flow along the coronary arteries during revascularization surgery (i.e., coronary artery by-pass surgery, CABG) it is termed Thermal Coronary Angiography (TCA). TCA is a technique that is capable of providing unique, clinically relevant information about epicardial coronary arteries and by-pass grafts in real-time during revascularization surgeries. See for example U.S. Pat. Nos. 4,995,398 and 5,375,603.

Among other applications, TCA is a method that was developed to replace some invasive methods for specific applications, imaging methods exploiting harmful contrast agents, and methods with other, such as, for example, accuracy, limitations, to estimate blood flow through the coronary arteries and by-pass grafts. These methods include arteriography in which a radiopaque dye is injected into the coronary arteries, which dye serving as a contrast agent; passage of coronary probes; electromagnetic flow measurements; angioscopy; and cine-angioscopy. Each of these methods has its specific limitations.

TCA involves injecting 20–30 ml of a cold substance, such as, for example, crystalloid cardioplegia, saline or blood, into, for example, the aortic root and, recording the temperature changes associated with, for example, the surface of the coronary arteries by a thermovision system. In cases where a beating heart is inspected, the temperature changes of the surface of the coronary arteries associated with warm blood replacing the cold substance may be recorded alternatively or additionally. Recordings can also be made of the surface of the heart tissue itself, which recordings reflect perfusion of the cold substance or of body temperature blood, into the heart tissue. Alternatively, if the flow of blood through the coronary arteries is artificially reduced or ceased completely for a given period of time, the epicardial temperature will drop to a minimal level close to the surrounding rooms temperature. Replenishing blood flow of body temperature blood at this point will elevate the epicardial temperature and a transient temperature response curves will, therefore, be available. In this case, as generally stated above, the blood, which is the substance which flow is measured, serves also as the thermo-contrast agent.

Thermography in open-chest conditions have been previously employed also for verification of graft patency (see, Mohr, et al. (1989) Thermal coronary angiography: a method for assessing graft patency and coronary anatomy in coronary bypass surgery. Ann. Thorac. Surg. (USA), 47(3):441–449.) and proper myocardial cooling during cardioplegia (see, Pantaleo et. al. (1984) Thermographic evaluation of myorardial cooling and intraoperative control of graft patency in patients with coronary artery disease. J. Cardiovasc. Surg. 25(6):554–559.). Assessment of blood perfusion by thermography of the myocardium was also reported (see, Adachi and Becker (1987) Assessment of myocardial blood flow by real-time InfraRed imaging. J. Surg. Res., 43(1):94–102. and Kekesi et. al. (1986) Hemodynamics and thermographic signs of intermyocardial venous outflow redistribution induced by coronary sinus occlusion in the canine heart. Acta. Chir. Hung., 27(4):203–15.). However, in all of these cases, and others, the kinetic (i.e., transient response) of the temperature from successive thermoimages was not deduced.

Furthermore, when TCA is employed in real-time, during by-pass surgeries, estimation of flow through the coronary arteries is based on visual inspection of the coronary tree as reflected by its thermal image, which visual inspection enables to observe a presence of narrow zones or blockages along the coronary arteries. Nevertheless, such visual inspection does not provide numerical data regarding the actual flow of substances along the coronary arteries.

It is an object of the present invention to provide tools for calculating flow rates of substances within objects by extracting and mathematically manipulating numerical parameters from thermoimaging transient temperature response curves of the surface of the objects.

SUMMARY OF THE INVENTION

According to the present invention there are provided methods for determining the flow rate of substances within objects, by extracting and mathematically manipulating numerical parameters from thermoimaging transient temperature response curves of the surface of the objects. The methods of the present invention are suitable to determine coronary arteries flow rates and myocardial perfusion rates in open chest conditions.

According to a preferred embodiment of the invention described below, the method is to determine a flow rate of a substance in an object, the object including a surface and an upstream region, comprising the steps of (a) providing the upstream region with a thermo-contrast agent; (b) obtaining successive thermoimages of at least a part of the surface of the object; (c) generating a temperature response curve from the thermoimages for at least a section of the surface being reflected in the thermoimages.

According to another embodiment the method is to determine a flow rate of a thermo-contrast agent in an object, the object including a surface and an upstream region, comprising the steps of (a) providing the upstream region with the thermo-contrast agent; (b) generating successive thermoimages of at least a part of the surface of the object; and (c) generating a temperature response curve from the thermoimages for at least a section of the surface being reflected in the thermoimages.

According to still further features in the described preferred embodiments the method further comprising extracting a parameter from the temperature response curve.

According to still further features in the described preferred embodiments the method further comprising determining the flow rate from the parameter.

According to still further features in the described preferred embodiments the parameter is the area above the temperature response curve.

According to still further features in the described preferred embodiments the parameter is the peak temperature difference.

According to still further features in the described preferred embodiments the parameter is the slope of the descending part of the temperature curve.

According to still further features in the described preferred embodiments the parameter is the exponential recline coefficient of the ascending part of the temperature curve.

According to still further features in the described preferred embodiments the exponential recline coefficient is calculated by a non-linear parameter estimation, for example, according to minimal least squares method.

According to still further features in the described preferred embodiments determining of the flow is by the exponential recline coefficient according to a heat-transfer model.

According to still further features in the described preferred embodiments the parameter is selected from the group of parameters consisting of time to peak, time to half decline, time to half recline, appearance disappearance time, time from peak to half recline, time from half decline to half recline and parameter alpha from a gamma-variant function.

According to still further features in the described preferred embodiments the object is an organ of a living object.

According to still further features in the described preferred embodiments the organ is a body organ.

According to still further features in the described preferred embodiments the body organ is selected from the group of body organs consisting of a heart and a coronary artery.

According to still further features in the described preferred embodiments the body is of a human.

According to still further features in the described preferred embodiments the object is a non-living object.

According to still further features in the described preferred embodiments the substance contains blood.

According to still further features in the described preferred embodiments the substance is selected from the group of substances consisting of blood, saline, crystalloid cardioplegia and combinations thereof.

According to still further features in the described preferred embodiments the thermo-contrast agent is cold relative to the substance.

According to still further features in the described preferred embodiments the thermo-contrast agent is cold relative to the object.

According to still further features in the described preferred embodiments the thermo-contrast agent is hot relative to the substance.

According to still further features in the described preferred embodiments the thermo-contrast agent is hot relative to the object.

According to still further features in the described preferred embodiments the substance is selected from the group of substances consisting of liquid substances, gas substances, solid substances and mixtures thereof.

According to still further features in the described preferred embodiments the thermo-contrast agent is selected from the group of thermo-contrast agents consisting of liquid thermo-contrast agents, gas thermo-contrast agents, solid thermo-contrast agents and mixtures thereof.

The present invention discloses novel methods to determine flow rates of substances within objects by manipulating thermoimages of the objects throughwhich the substances are flowing.

More specifically, the methods of the present invention are used to determining flow rates of substances by extracting and mathematically manipulating numerical parameters from thermoimaging temperature response curves. Therefore, the methods of the present invention may be used to determine coronary flow and myocardial perfusion in a non-invasive manner.

BRIEF DESCRIPTION OF THE DRAWINGS

The invention is herein described, by way of example only, with reference to the accompanying drawings, wherein:

FIG. 3 is a transient temperature response curve of the average epicardial coronary temperature.

FIG. 4 is a presentation of the area above the temperature response curve shown in FIG. 3;

FIG. 10 is a presentation of the relationship between the estimated value of k and coronary flow. Each symbol (o, x, +, =, *) represents the result of a certain experiment (dog).

DESCRIPTION OF THE PREFERRED EMBODIMENTS

Figure 1:
FIG. 1 is a thermograph obtained at maximal cooling of the coronary tree.

The present invention is of methods for determining flow rates of substances by thermoimaging which can be used to calculate flow rates of substances within objects by extracting and mathematically manipulating numerical parameters from thermoimaging transient temperature response curves (i.e., temperature kinetic curves generated thermoimagically). Specifically, the present invention is suitable to determine coronary flow rates and myocardial perfusion rates in open chest conditions, that is, to calculate flow rates of substances along the coronary arteries and, myocardial perfusion rates of substances into the heart tissue.

The principles and operation of methods for determining flow rates of substances by thermoimaging, according to the present invention, may be better understood with reference to the Figures and the accompanying description.

Availability of real-time information regarding coronary flow and myocardial perfusion may be of great value for the cardiac surgeon. Applying thermography for this purpose provides the option of imaging the coronary tree during surgery, devoid of the need of harmful contrast agent injections.

Thermography in open-chest conditions have been previously employed for identification of damaged zones in the coronary arteries, verification of graft patency, proper myocardial cooling during cardioplegia and, assessment of blood perfusion by thermography of the myocardium.

It is one objective of the present invention to identify measures (i.e., parameters) suitable for flow rate determination by analyzing transient temperature response curves, obtained thermographically.

It is a specific object of the present invention to identify measures (i.e., parameters) suitable for epicardial coronary flow rate determinations by analyzing epicardial temperature response curves obtained thermographically.

For this purpose a model system was set up. Five dogs were anesthetized by Nembutal, each dogs chest was opened by left thoracotomy, the pericardium opened and the heart was suspended in the pericardial cradle. An ultrasonic transit time flowmeter was placed on the proximal left anterior descending artery (LAD) and an injection catheter was placed in the aortic root. Agema camera (Thermovision 900 system), which provides a temperature resolution of 0.1° C. and a spatial resolution of 0.75 mm, was located 43 cm above the exposed heart. The epicardial temperature image was continuously visualized on a screen. As recording began, end-diastolic images were stored for further analysis by an electrocardiogram-R-wave (EGG-R-wave) triggering of the thermography system, to minimize cardiac motion artifacts. The respiration was suspended immediately prior to recording, in order to minimize cardiac motion effect. Several seconds after recording was started, a 20 cc of saline at 0° C. was injected through the catheter into the aortic root. Recording was continued for 20–30 seconds post the injection. Data were acquired at several flow levels achieved by one minute LAD occlusion, which induced reactive hyperemia.

Referring now to the drawings, FIG. 1 illustrates a typical image of maximal cooling of the coronary tree as described hereinabove. In this image a partial visualization of the coronary tree 20, the left anterior descending artery 22 and its diagonal branches 24 are well visualized.

Figure 2:
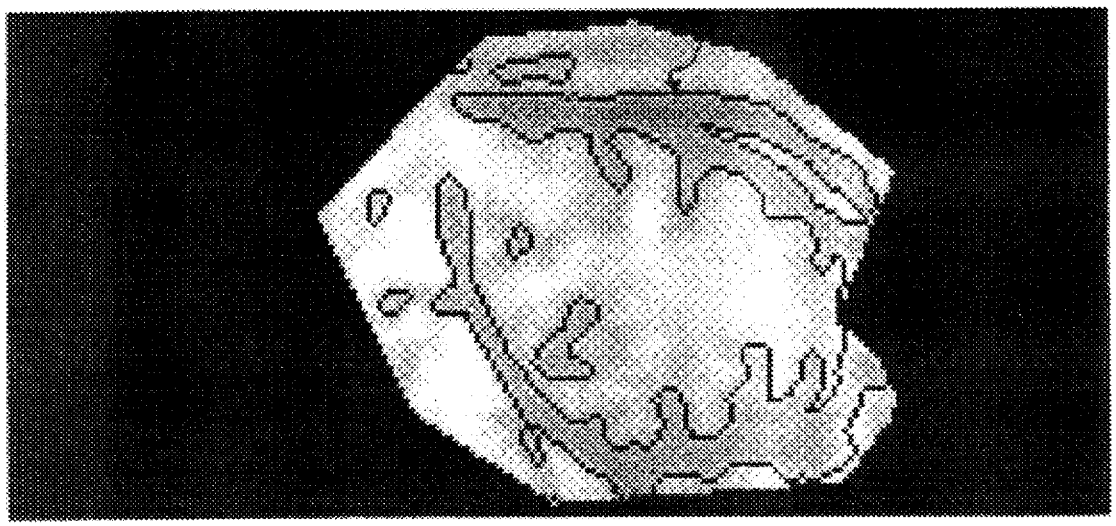
FIG. 2 is a the coronary arteries edges window, superimposed on the maximum cooling image shown in FIG. 1 (blackened area eliminates non-epicardial objects)

For each injection, the edges of the coronary tree of the image of maximal cooling (e.g., the image shown in FIG. 1) were detected by an edge detection algorithm and were superimposed on all other recorded images obtained subsequent to the injection. The window 26 surrounding the coronary tree, produced by the edge detection algorithm, superimposed on the image from which it was extracted, is shown in FIG. 2.

The window surrounding the coronary tree can be determined otherwise by, for example, superimposing the thermoimage on a visible light photograph of the epicardium made to the same scale and angle.

Using the edge detected window, the average temperature of the coronary tree surface was calculated for each image frame, and the temperature of the coronary tree surface was plotted as a function of the time, generating a transient temperature response curve. A typical result of a transient response of the average epicardial coronary surface temperature as measured by thermoimaging (i.e., a transient temperature response curve) is shown in FIG. 3.

Transient temperature response curves, similar in their general appearance to the one shown in FIG. 3, were previously generated employing thermodilution methods for determining flow rates. Yet, as mentioned above, thermodilution is an invasive method in which a temperature detection probe is made in direct contact with a substance which flow is to be determined. However, this is the first time where transient temperature response curves are extracted from thermoimages data.

It will be appreciated by one ordinarily skilled in the art that similar transient temperature response curves can be extracted from a selected region or regions of the coronary tree to, as will be detailed below, extract numerical parameters, from which a determination of flow rates can be made. It is further understood that similar curves can be obtained for the heart itself reflecting transient temperature response of the heart surface due to perfusion of substances into the heart. It is still further understood that such curves can be similarly obtained from any other organ of living creatures such as humans, animals and plants. It is also understood that similar curves can be obtained from non-living objects.

According to the present invention, several methods for flow rates determination, employing numerous parameters extracted from transient temperature response curves generated from thermoimages, are disclosed. At present the use of the methods of the present invention are selected for coronary arteries flow rate determinations, therefore, most of the examples described hereinbelow refer to coronary arteries flow rate determinations. Nevertheless, it is understood that the methods of the present invention may be of use in other medical and non-medical fields as well.

For clarification of terms used hereinbelow and in the claims thereafter, it should be noted that the transient temperature response curve, shown, for example, in FIG. 3, is obtained using a cold thermo-contrast agent, therefore the peak of the curve is at a curve minimum, representing the lowest temperature. Such curves are referred to as minimum curves. Nevertheless, when using a hot thermo-contrast agent, or alternatively, when the Y axis is reversed, a reversed, maximum curves are obtained. As a matter of convenience, the terms used hereinbelow, which terms refer to specific phases of the curves, were literally selected to describe a minimum curve, yet, it is the intention that in this document these terms will reflect also the corresponding terms describing a maximum curve. For example, when the area above the curve is specified hereinbelow for a minimum curve, it also specifies the area under the curve for a maximum curve; or, when the terms decline (descending) or recline (ascending) are specified hereinbelow, they refer to the decline (descending) or recline (ascending) phases of a minimum curve and also to the recline (ascending) or decline (descending) phases of a maximum curve, respectively; or, when a minimal temperature is specified for a minimum curve it also specifies a maximal temperature for a maximum curve.

(1) The area above the transient temperature response curve:

A mathematical description of the area above the transient temperature response curve, shown marked in FIG. 4, according to thermodilution methods, wherein C is a constant; T is the temperature; and t is the time, is given in Equation 1.

Equation 1:

$$\int_0^\infty C(T)dt$$

The correlation between this parameter, the amount of cold indicator (e.g., cold saline) (m) and the flow (F), as was determined for thermodilution methods (see, Meier and Zierler (1954) On the theory of the indicator-dilution method for measurement of blood flow and volume. Journal of Applied Physiology 6(12), 731–744.) is given in Equation 2.

Equation 2:

$$m = F\int_0^\infty C(T)dt$$

Nevertheless, when a beating heart is analyzed, as coronary flow increases, a larger portion of the cold saline provided by injection enters the coronary arteries and vice versa. Therefore, the use of a dilution method principle, which principle assumes a constant amount of upstream indicator, is not appropriate in the case described hereinabove wherein a beating heart is analyzed, since the amount of cold saline that enters the coronary arteries is (1) unknown, since an unknown fraction of it may spread from the aortic root to the body while mixing with the blood and, (2) dependent upon the blood flow in the coronary arteries, itself. Therefore, it is not surprising that under the above described experimental conditions (i.e., a beating heart), a relatively weak correlation between the area above the transient temperature response curve and the flow (as measured independently by the flowmeter) was obtained, $r=0.55$, $p<0.02$, in a total of five dogs.

Nevertheless, in a case where a known amount of a thermo-contrast agent is injected directly into the artery or into a graft, the above described limitations are eliminated and, a higher correlation between the area above the transient temperature response curve and the flow is expected.

Figure 5:
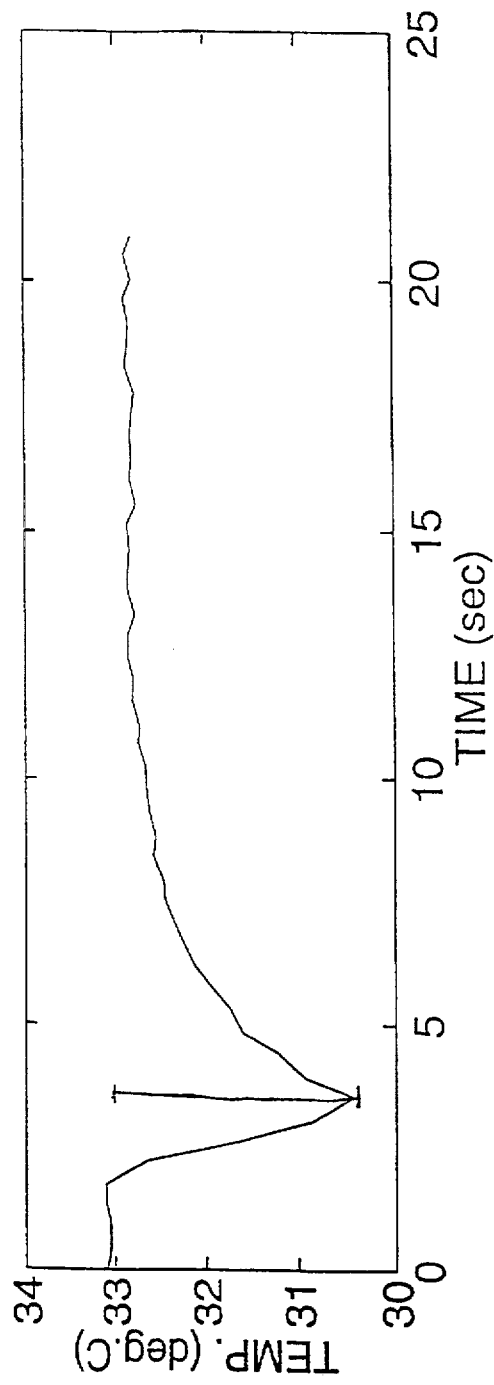
FIG. 5 is a presentation of the peak temperature difference in the transient temperature response curve of FIG. 3.

(2) The peak temperature difference:

The peak temperature difference is, as shown in FIG. 5, the difference between the minimal and the initial temperature. As more cold saline enters the coronary arteries due to increased flow, the larger the gradient for heat-transfer is, resulting in a larger peak temperature difference as determined thermographically. Therefore, a better correlation with flow was obtained using the peak temperature difference parameter ($r=0.71$, $p<0.001$) than using the area above the transient temperature response curve, as described hereinabove.

However, it will be appreciated by one ordinarily skilled in the art that while injecting the thermo-contrast agent directly to a coronary artery or a graft, the amount of cold saline that enters the coronary arteries or the graft is known. Therefore, a higher correlation between the peak temperature difference of the transient temperature response curve and flow rates is expected under these circumstances.

Figure 6:
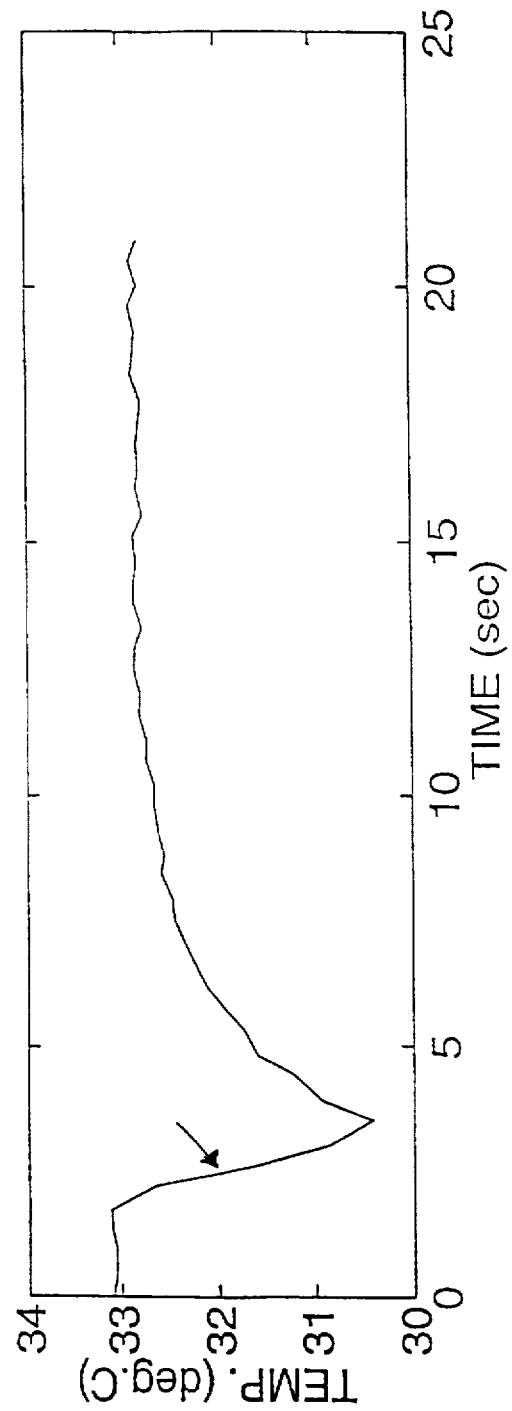
FIG. 6 is a presentation of the slope of the descending part of the transient temperature response curve shown in FIG. 3.

(3) The slope of the descending part of the temperature curve:

The slope of the descending part of the temperature curve, as shown in FIG. 6, is influenced by the magnitude of the temperature gradient and, thus, by the flow. Its correlation with flow, as measured under the above described conditions is $r=0.64$, $p<0.002$.

However, similarly to the described above, it is understood that while injecting the thermo-contrast agent directly to a coronary artery or a graft, a higher correlation between the slope of the descending part of the transient temperature response curve and flow rates is expected.

The three parameters thus described, the area above the temperature response curve, shown in FIG. 4; The peak temperature difference, shown in FIG. 5; and the slope of the descending part of the temperature curve, shown in FIG. 6, present reasonable to low correlation with the flow as independently measured, when extracted from transient temperature response curves of beating hearts, injecting the thermo-contrast agent to the aortic root. This is most likely due to variations in the amount of cold saline entering the coronary arteries in different experimental trials. While working with a beating heart, blood is rhythmically pumped by the heart from the lungs and transferred by the heart into the aorta. From the aorta, part of the blood is transferred to the coronary arteries which supply the heart tissue with blood and, the rest is transferred to the rest of the body. The part transferred to the coronary arteries may vary to a great extent even between one heart beat to the one following it, depending on various factors, such as, for example, the body blood pressure. The injection process itself prolongs ca. three seconds (several heart beats). Therefore, the amount of cold saline entering the arteries varies tremendously among separate injections. Since the amount of cold saline entering the arteries depend on various parameters additionally to the flow, the correlation results of these three parameters with flow rates are less satisfactory.

Nevertheless, in a different situation, when the amount of the thermo-contrast agent entering the arteries (or a graft) is known, these parameters are expected to be correlated with the flow rate to a greater extent. Therefore, determining the area above the temperature curve, the peak temperature difference and the slope of the descending part of the temperature curve is of great value to determine flow rates and, hence, suggested according to the present invention to be used, for example, during artery by-pass surgeries, to determine flow rates before (e.g., in the narrowed coronary arteries) and after (e.g., in the graft(s)) the operation.

It is further suggested that the above mentioned parameters are to be used to determine flow rates in other parts of the body, such as, for example, the brain and, in non-living systems, such as, for example, in systems including tubings throughwhich substances are flowing.

Figure 7A:
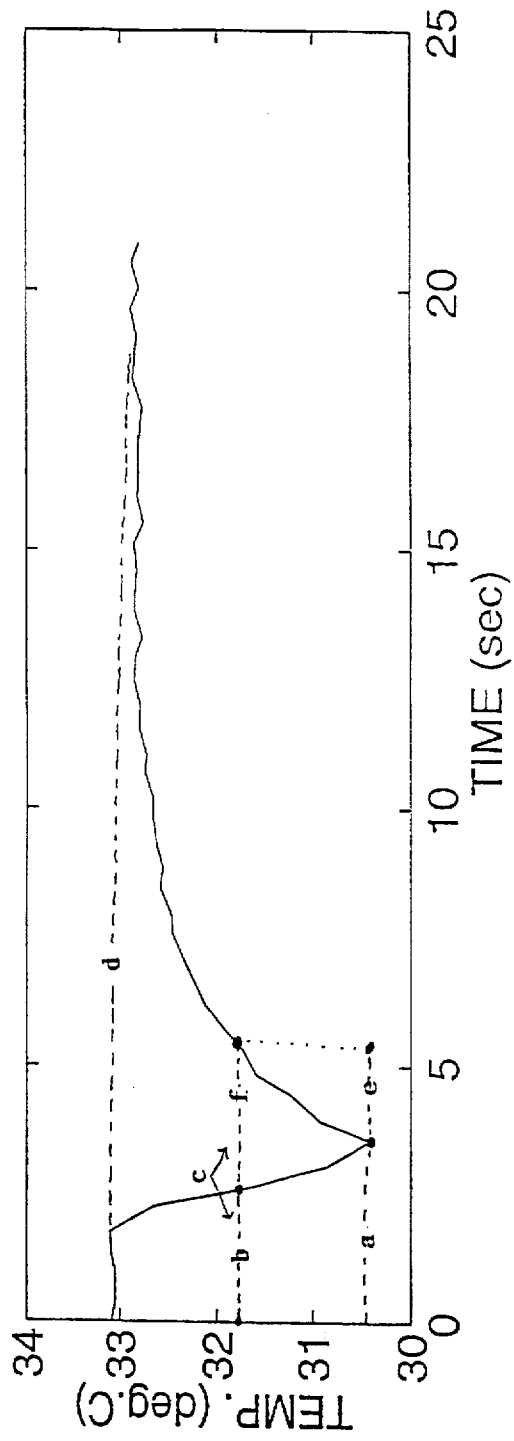
FIGS. 7a and 7b are presentations of additional parameters of the transient temperature response curve shown in FIG. 3 and a reversed curve similarly generated when a hot substance is used a contrast agent.
Figure 7B:
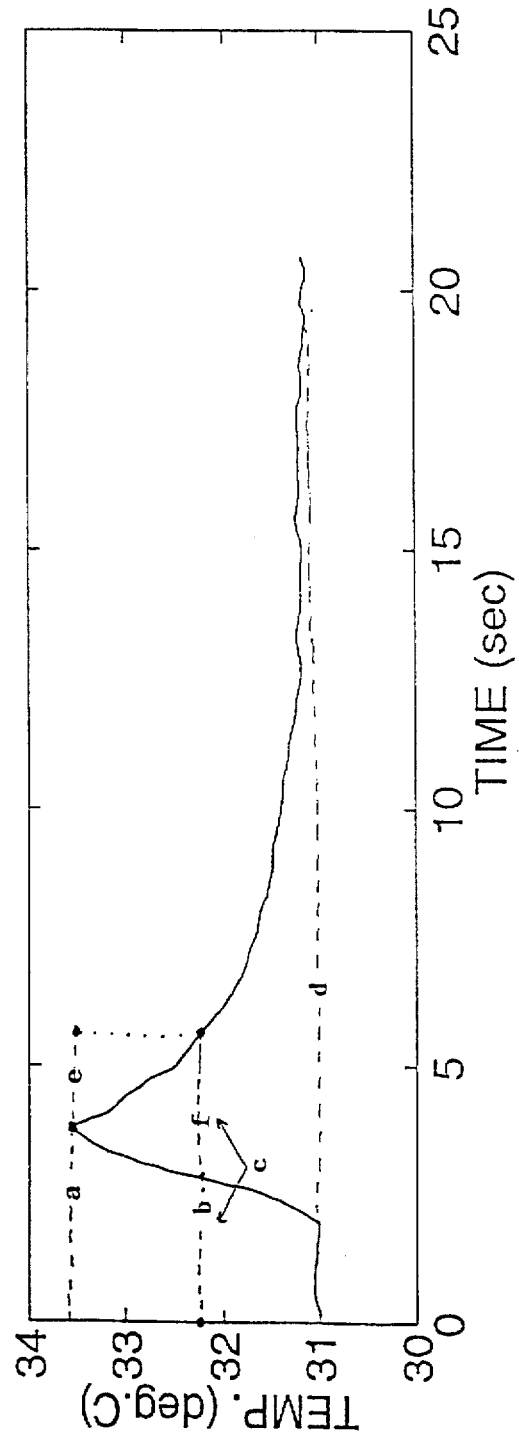

(4) Additional parameters:

Additional parameters have been extracted from transient response curves generated using thermodilution and other methods for flow determination and may be applied, as shown in FIGS. 7a–b, to transient temperature response curves generated thermoimagically. These parameters include: (a) time to peak, a in FIG. 7a; (b) time to half decline, b in FIG. 7a; (c) time to half recline, c in FIG. 7a; (d) appearance disappearance time, d in FIG. 7a; (e) time from peak to half recline, e in FIG. 7a; (f) time from half decline to half recline, f in FIG. 7a; (g) parameter alpha from a gamma-variant function. See, for example, Ten Cate (1984) Myocardial contrast two-dimentional echocardiography: experimental examination at different coronary flow levels. JACC 3(5), 1219–26; Rovai et al. (1992) Myocardial washout of sonicated iopamidol reflects coronary blood flow in the absence of autoregulation. JACC 20(6),1417–24; Cheirif et al. (1989) Assessment of regional myocardial perfusion by contrast echocardiographys. II. Detection of changes in transmural and subendocardial perfusion during dipyridamole-induced hyperemia in a model of critical coronary stenosis. JACC 14(6), 1555–65; Kaul et at. (1989) Assessment of regional myocardial blood flow with myocardial contrast two-dimentional echocardiography. JACC 3(2),468–82; Rumberger (1987) Use of ultrafast computed tomography to quantitate regional myocardial perfusion: a preliminary report. JACC 9(1), 59–69.

While this description is applicable when a cold substance is traced, as shown in FIG. 7b, the curve inverses when a hot substance is employed as a thermo-contrast agent and, similar parameters may be extracted from the inversed curve, as also delineated above.

The parameters, shown in FIGS. 7a–b, and additional parameters that may be extracted from transient temperature response curves generated using thermoimaging, are herein suggested for the first time to be correlated to flow rates. Hence, it is an object of the present invention to determine flow rates by mathematically manipulating any specific and/or any combination of parameters that can be extracted from transient temperature response curves generated using thermoimaging methods.

Figure 8:
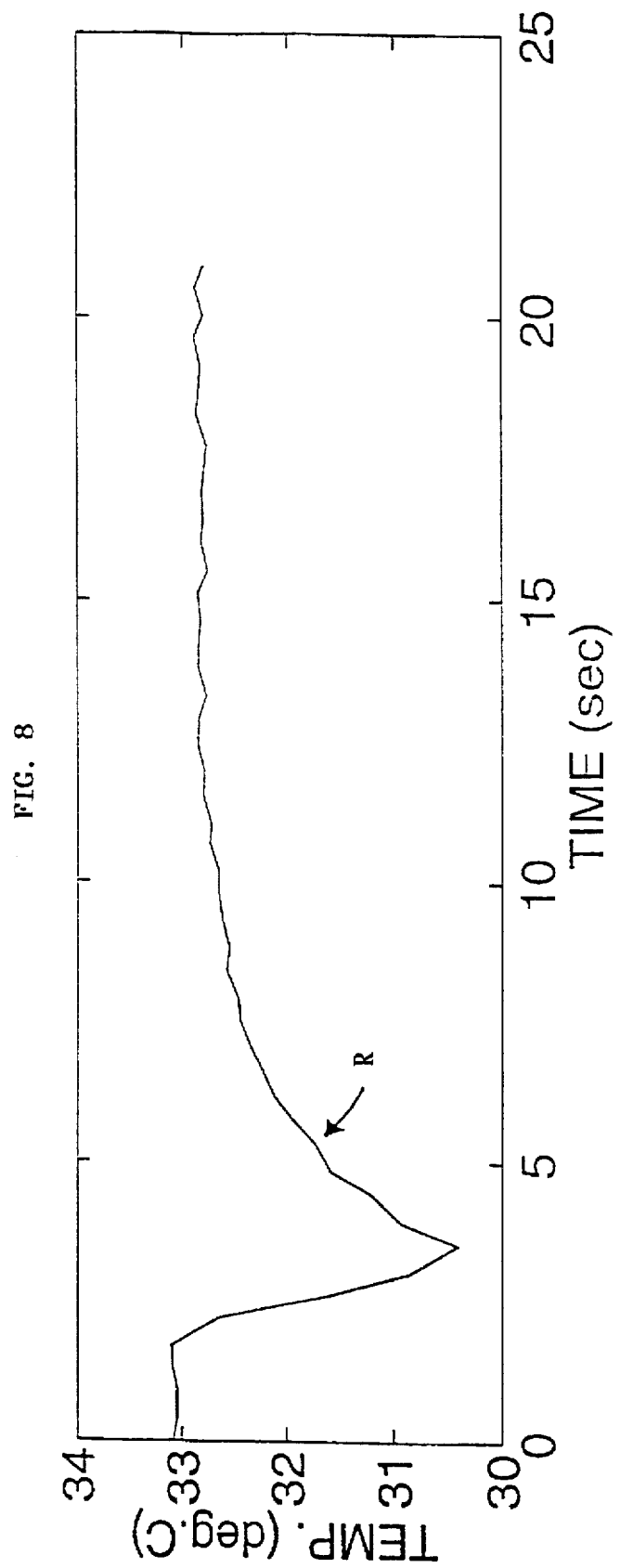
FIG. 8 is a presentation of the slope of the ascending part of the transient temperature response curve shown in FIG. 3.

(5) The slope of the ascending part of the temperature response curve:

The slope of the ascending part of the transient temperature response curve, shown in FIG. 8, depend on the temperature and flow rate of warm blood replacing the cold saline and, therefore, this parameter may be extracted only when beating hearts are analyzed. Nevertheless, the slope of the ascending part of the transient temperature response curve is not dependent upon the amount of cold saline entering the arteries in any individual experimental trial. One can ignore the causes for this minimal temperature and consider the situation as a simple case of heat-transfer by convection. This requires the assumption that the coronary tree is of lumped heat capacity, namely, the temperature distribution within the artery walls is homogeneous.

According to the heat-transfer theory (i.e., model), the common criterion for assuming lumped heat capacity, wherein h is the convective heat-transfer coefficient, V is the volume of the entire exposed epicardial arterial wall, A is its surface area in contact with the blood and, k is the conduction heat-transfer coefficient, is:

Equation 3:
$$Bi = \frac{h(V\backslash A)}{k} < 0.1$$

Nevertheless, considering the thin artery wall, V is relatively small compared to A, hence, the ratio (V/A) is very small. Therefore, a simple assumption of convective heat-transfer in a lumped heat-capacity coronary tree is reasonable, where the initial temperature and the fluid temperature are known. This assumption is herein suggested for the first time.

An alternative criterion to assume lumped heat-capacity is a high heat conductivity of the walls.

The heat-transfer equation for this case is given by Equation 4, wherein, ρ is the arterial tree wall density, c is its specific heat, T is its average temperature, h is the heat-transfer convective coefficient which varies with v, which is the flow velocity, $T_b$ is the blood temperature and, t is the time:

Equation 4:

$$\rho c V \frac{dT(t)}{dt} = h(v)A(T_b - T(t))$$

The solution of Equation 4 is given in Equation 5, wherein k is the exponential recline coefficient which varies with v:

$$T(t)=T_b-(T_b-T_0)e^{-k(v)t} \qquad \text{Equation 5}$$

k(v), therefore, equals (Equation 6):

Equation 6:

$$k(v) = \frac{h(v)A}{\rho c V}$$

Figure 9A:
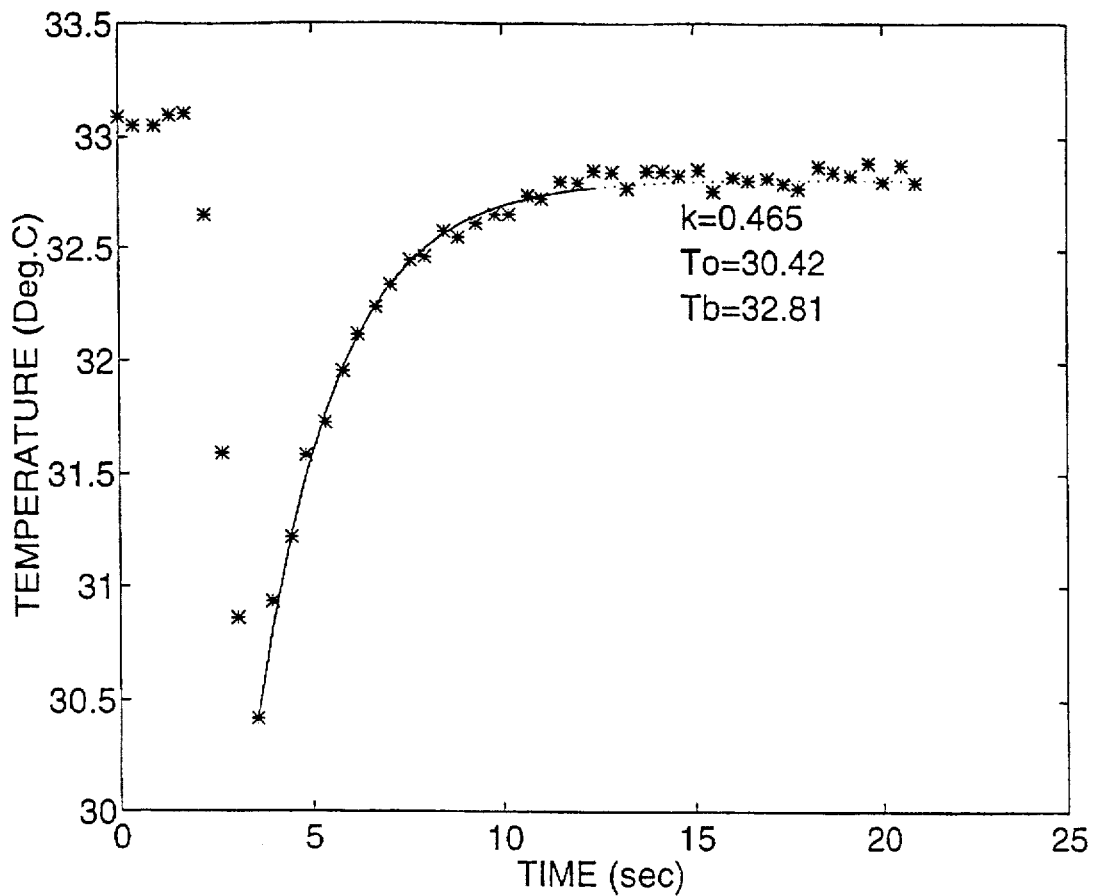
FIGS. 9a and 9b present an estimation of the exponential decline coefficient k(v) and the other heat-transfer model parameters by a non-linear parameter estimation according to minimal least squares.
Figure 9B:
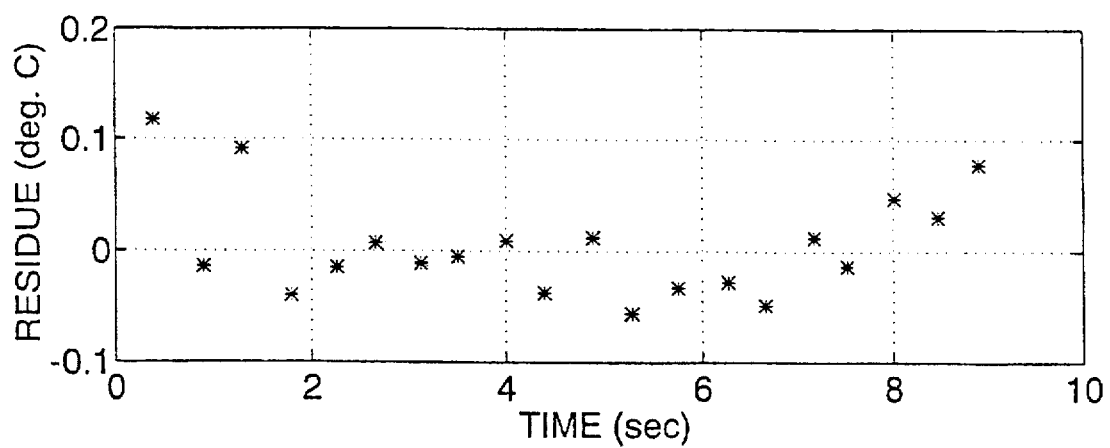

Estimation of k(v) and the other heat-transfer model parameters by the conventional parameter-estimation methods known as non-linear parameter estimation, for example, according to minimal least squares (non-linear MLS), is shown in FIGS. 9a–b.

Referring now to FIG. 9a, the calculated non-linear MLS results are shown in a continuos line at the range that was used for fitting, whereas the dashed line represents an extrapolation of this fit for the rest of the data. The asterisks denote the data obtained thermografically as described hereinabove. Referring now to FIG. 9b, it can be seen that the residues are small and are of a random nature, therefore, indicating that the heat-transfer model is appropriate for description of the major mechanism of the temperature response in the ascending part of the transient temperature response curve generated thermographically.

The results described above, shown in FIG. 9a, were obtained by constrained non-linear parameter estimation of all the heat-transfer model parameters, including $T_0$ and $T_b$.

The relation of k(v) vs. flow (as measured independently), calculated for four dogs using linear parameter estimation according to minimal least squares (linear MLS) of k is presented in FIG. 10.

It can be shown, based on the analysis presented by Ozisik (see, Ozisik. Heat-transfer—a basic approach. New York: McGraw-Hill, 1985.), that indeed in this case h depends solely on the flow velocity (Equation 7).

$$h=f(v) \qquad \text{Equation 7}$$

Figure 11:
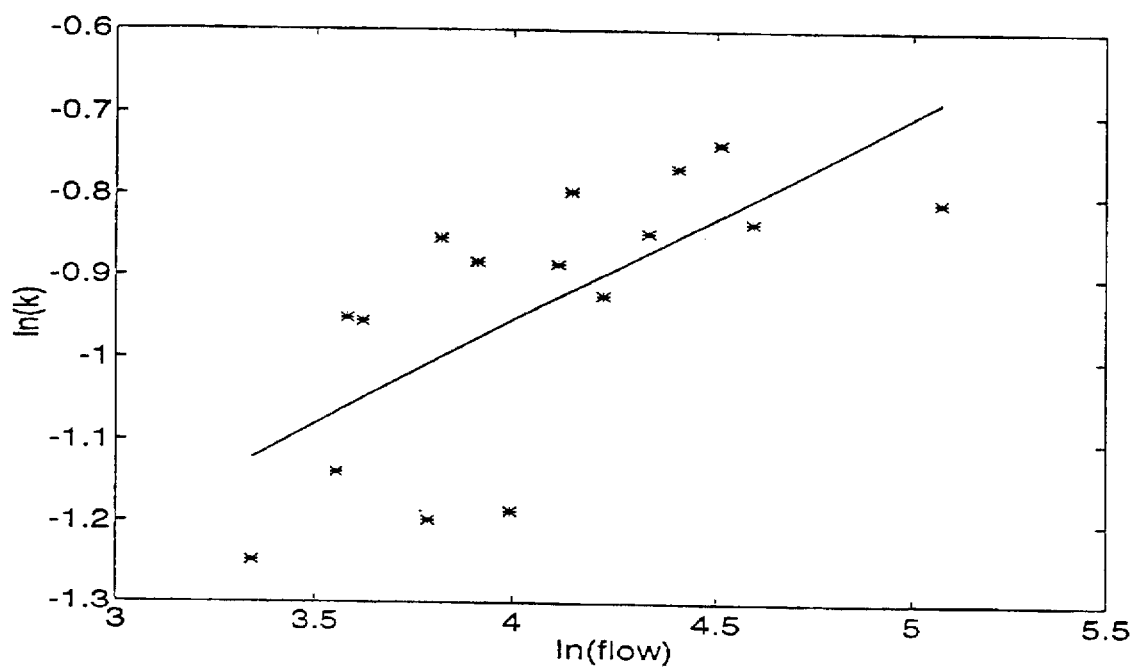
FIG. 11 is a presentation of lnk as a function of ln(flow). The continuos line denotes the linear fit for the experimental data.

Assume that (Equation 8), $$h=a \cdot v^n \qquad \text{Equation 8}$$

which is a common assumption in heat-transfer theory, concluding that (Equation 9), $$k=a \cdot flow^n \qquad \text{(Equation 9)}$$

where, $k \propto$ ch , flow$\propto$v
Fitting Equation 9 to the data, by linearization (Equation 10), $$\ln(k)=\ln(a)+n \cdot \ln(flow) \qquad \text{Equation 10}$$

results in the graph presented in FIG. 11. The results of the fit are: a=0.1411, n=0.2511, and the correlation with flow: r=0.69, p<0.005.

Based on these results, it is suggested herein, for the first time, that a correlation between the exponential recline coefficient (k) of the ascending part of the transient temperature response curve generated thermographically and flow rate exists and, therefore, k, which, as shown in FIG. 9a–b, can be estimated solely by a non-linear MLS of temperatures determined thermographically, can be used to determine flow rates.

It should be noted that the correlation of k with the flow on a logarithmic scale (FIG. 11) was based on an analysis which employed a linear parameter estimation method (e.g., linear MLS). The result when applying non-linear estimation (e.g., non-linear MLS) may be better than the linear estimation, since theoretically the linearization affects the residues statistics, and thus divert the estimation. In accordance with the theory presented, an improvement in the correlation of k with the flow is expected after applying the more elaborated constrained non-linear method for k estimation.

Extracting k from a thermografically generated transient temperature response curve and determining blood flow rates along the coronary arteries can be made during heart surgeries prior to stilling the heart. Similarly, blood perfusion rates from the coronary arteries into the heart tissue can be made as well. Hence, the average coronary epicardial temperature response to cold saline injections can be used for determination of coronary blood flow.

Furthermore, extracting k from a thermografically generated transient temperature response curve and determining flow rates can be made in any living or non living system characterized by an intrinsic flow of any substance(s), which substances may be liquid substances, gas substances, solid substances and mixtures thereof.

It will be appreciated by one ordinarily skilled in the art, that similar analyses, that is, extracting various numerical parameters and determining flow rates can be similarly made from inversed transient temperature response curves generated thermographically using a hot substance as a thermo-contrast agent.

It is further understood that when a flow is determined according to the methods of the present invention, the thermo-contrast agent may be the flowing substance itself. For example, if the flow of blood through the coronary arteries is artificially reduced or ceased completely for a given period of time, the epicardial temperature will drop to a minimal level close to the rooms temperature. Replenishing blood flow of body temperature blood at this point will elevate the epicardial temperature and a transient temperature response curves will, therefore, be available. In this case, as generally stated above, the blood, which is the substance which flow is measured, serves also as the thermo-contrast agent. Therefore, when the phrase 'providing the upstream region with a thermo-contrast agent', is used hereinbelow in the claims, it refers to this situation as well.

Similarly, when an object (e.g., a still heart) is characterized by an internal flow rate which equals zero, alternatively, when the object does not include a substance all together, the flow of a provided thermo-contrast agent can be determined according to the method of the present invention, using some of the parameters described above. Nevertheless, in this case, parameters which take into account the ascending part of the transient temperature response curve (e.g., the area above the curve, time to half recline, appearance disappearance time, time from peak to half recline and time from half decline to half recline) are irrelevant, since, in this case the curve will rich a minimum which will sustain a prolonged time.

The average coronary epicardial temperature response to cold (or hot) substance injections can be used for determination of coronary blood flow. Reasonable correlations between the coronary flow of a beating heart and the transient temperature response were achieved by the methods of peak temperature difference and of the heat-transfer model. Additional parameters extracted from the average coronary epicardial temperature response to cold (or hot) substance injections can be used for determination of coronary flow in a still heart.

Therefore, coronary flow can be determined using cardiac thermography, employing image processing and transient temperature response analysis. For future applications, the method of the present invention provides a tool which will provide the surgeon with real-time epicardial flow information.

In addition, the present invention provides methods for determining flow rates of substances within objects by extracting and mathematically manipulating numerical parameters from transient temperature response curves generated from thermoimages of the surface of the objects.

While the invention has been described with respect to a limited number of embodiments, it will be appreciated that many variations, modifications and other applications of the invention may be made.

What is claimed is:

1. A method for determining a flow rate of a substance in an object, the object including a surface and an upstream region, comprising the steps of:
   (a) providing the upstream region with a thermo-contrast agent;
   (b) obtaining successive thermoimages of at least a part of the surface of the object;
   (c) generating a temperature response curve from said thermoimages for at least a section of the surface being reflected in said thermoimages;
   (d) extracting a parameter from said temperature response curve; and
   (e) determining said flow rate from said parameter.

2. A method as in claim 1, wherein said parameter is the area above said temperature response curve.

3. A method as in claim 1, wherein said parameter is the peak temperature difference.

4. A method as in claim 1, wherein said parameter is the slope of the descending part of said temperature curve.

5. A method as in claim 1, wherein said parameter is the exponential recline coefficient of the ascending part of said temperature curve.

6. A method as in claim 5, wherein said exponential recline coefficient is calculated by a non-linear parameter estimation.

7. A method as in claim 6, wherein said determining of said flow is by said exponential recline coefficient according to a heat-transfer model.

8. A method as in claim 1, wherein said parameter is selected from the group of parameters consisting of time to peak, time to half decline, time to half recline, appearance disappearance time, time from peak to half recline, time from half decline to half recline and parameter alpha from a gamma-variant function.

9. A method as in claim 8, wherein said organ is a body organ.

10. A method as in claim 9, wherein said body organ is selected from the group of body organs consisting of a heart and a coronary artery.

11. A method as in claim 9, wherein said body argon is of a human.

12. A method as in claim 11, wherein said body organ is selected from the group of body organs consisting of a heart and a coronary artery.

13. A method as in claim 1, wherein said object is an organ of a living object.

14. A method as in claim 1, wherein said object is a non-living object.

15. A method as in claim 1, wherein said substance contains blood.

16. A method as in claim 1, wherein said thermo-contrast agent is cold relative to said substance.

17. A method as in claim 1, wherein said thermo-contrast agent is hot relative to said substance.

18. A method as in claim 1, wherein said substance is selected from the group of substances consisting of liquid substances, gas substances, solid substances and mixtures of liquid substances, gas substances and solid substances.

19. A method as in claim 1, wherein said thermo-contrast agent is selected from the group of thermo-contrast agents consisting of liquid thermo-contrast agents, gas thermo-contrast agents, solid thermo-contrast agents and mixtures of liquid thermo-contrast agents, gas thermo-contrast agents and solid thermo-contrast agents.

20. A method for determining a flow rate of a thermo-contrast agent in an object, the object including a surface and an upstream region, comprising the steps of:
   (a) providing the upstream region with the thermo-contrast agent;
   (b) generating successive thermoimages of at least a part of the surface of the object;
   (c) generating a temperature response curve from said thermoimages for at least a section of the surface being reflected in said thermoimages;
   (d) extracting a parameter from said temperature response curve; and
   (e) determining said flow rate from said parameter.

21. A method as in claim 20, wherein said parameter is the area above said temperature response curve.

22. A method as in claim 20, wherein said parameter is the peak temperature difference.

23. A method as in claim 20, wherein said parameter is the slope of the descending part of said temperature curve.

24. A method as in claim 20, wherein said parameter is the exponential recline coefficient of the ascending part of said temperature curve.

25. A method as in claim 24, wherein said exponential recline coefficient is calculated by a non-linear parameter estimation.

26. A method as in claim 25, wherein said determining of said flow is by said exponential recline coefficient according to a heat-transfer model.

27. A method as in claim 20, wherein said parameter is selected from the group of parameters consisting of time to peak, time to half decline, time to half recline, appearance disappearance time, time from peak to half recline, time from half decline to half recline and parameter alpha from a gamma-variant function.

28. A method as in claim 20, wherein said object is an organ of a living object.

29. A method as in claim 28, wherein said organ is a body organ.

30. A method as in claim 29, wherein said body organ is of a human.

31. A method as in claim 30, wherein said body organ is selected from the group of body organs consisting of a heart and a coronary artery.

32. A method as in claim 28, wherein said body organ is selected from the group of body organs consisting of a heart and a coronary artery.

33. A method as in claim 20, wherein said object is a non-living object.

34. A method as in claim 20, wherein said substance is selected from the group substances consisting of blood, saline, crystalloid cardioplegia and any combination of blood, saline and crystalloid cardioplegia.

35. A method as in claim 20, wherein said thermo-contrast agent is cold relative to said object.

36. A method as in claim 20, wherein said thermo-contrast agent is hot relative to said object.

37. A method as in claim 20, wherein said thermo-contrast agent is selected from the group of thermo-contrast agents consisting of liquid thermo-contrast agents, gas thermo-contrast agents, solid thermo-contrast agents and mixtures of liquid thermo-contrast agents, gas thermo-contrast agents and solid thermo-contrast agents.

* * * * *